United States Patent [19]

Selby

[11] 4,371,736
[45] Feb. 1, 1983

[54] HERBICIDAL PYRIDINYLOXY(PYRIMIDINYLOXY)BENZENES

[75] Inventor: Thomas P. Selby, Hockessin, Del.

[73] Assignee: E. I. Du Pont de Nemours and Company, Wilmington, Del.

[21] Appl. No.: 248,345

[22] Filed: Mar. 27, 1981

[51] Int. Cl.³ ............... C07D 239/32; A01N 43/40
[52] U.S. Cl. .................................. 544/316; 546/275; 546/276; 71/92; 71/94
[58] Field of Search ............... 546/276, 275; 71/94, 71/92; 544/316

[56] References Cited

U.S. PATENT DOCUMENTS 4,248,618  2/1981  Serban et al. ................ 544/316
4,248,619  2/1981  Serban et al. ................ 71/92

Primary Examiner—Nicholas S. Rizzo

[57] ABSTRACT

This invention relates to pyridinyloxy(pyrimidinyloxy)-benzene derivatives, herbicidal compositions containing them as active ingredient and to methods of using the compounds to control undesirable vegetation.

8 Claims, No Drawings

HERBICIDAL PYRIDINYLOXY(PYRIMIDINYLOXY)BENZENES

BACKGROUND OF THE INVENTION

This invention relates to certain pyridinyloxy-(pyrimidinyloxy)benzene derivatives which exhibit pre-emergence and post-emergence control of grasses and broadleaf weeds with safety to crops such as corn. More particularly, this invention relates to compounds such as 5-chloro-2-[2-(5-chloropyridin-2-yloxy)-phenoxy]-pyrimidine and to a process for their preparation.

Australian Pat. No. 005412 (European patent application No. 79301533.0) to ICI Australia Ltd. discloses the following bis(pyrimidyloxy)benzene derivatives as pre-emergent and post-emergent herbicides.

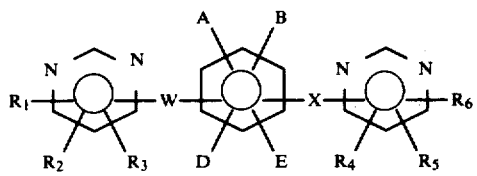

wherein
A, B, D and E are H, halogen, $NO_2$, CN, CNS, HCO, $SO_3H$, alkoxysulphonyl, YR, COYR, alkyl, alkenyl, cycloalkyl, alkylcarbonyl, $NH_2$, Ph, carbamoyl or sulphamoyl;
Y is O or S;
R is H, cation of inorganic or organic base;
$R_1$–$R_6$ are H, halogen, OH, $NO_2$, CN, CNS, $CO_2H$, alkoxycarbonyl, alknyloxy, alkylthio, cycloalkyl, $NH_2$, Ph, carbamoyl or sulphonyl; and
W is O or S.
Compounds represented by the following structure are included in the Australian Patent.

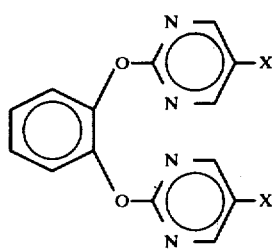

where X=Br or Cl.

United Kingdom application No. 7843037 to Ciba-Geigy discloses and claims a process for preparing hydroxydiarylethers which can be used as intermediates for preparing (phenoxy-phenoxy)alkanecarboxylic acids which have herbicidal and plant growth regulating action. The process comprises reacting a diether in a polar aprotic solvent in the presence of 0.1 to 1 mole of alkali per mole of diether to give a hydroxybenzene according to the following equation:

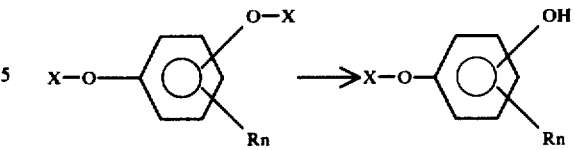

wherein
R is an alkyl group of 1–4 carbon atoms or Cl;
X is a phenyl group of the structure

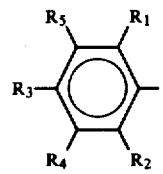

or a 2-pyridinyl group or a 4-pyridinyl group of the structure

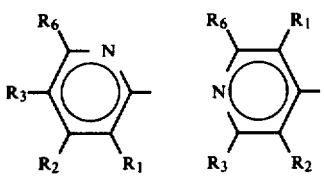

where $R_1$–$R_6$ are H, alkyl, Ph, halogen, $CF_3$, $NO_2$ or CN.

European patent application No. 78300378.3 assigned to ICI Australia Limited (priority Sept. 13, 1977, AU 162677) discloses 2-phenoxy and 2-phenylthio pyrimidines and their use as pesticides.

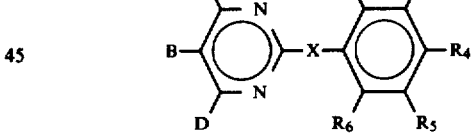

A, B and D are H, halogen, hydroxy, nitro, cyano, thiocyano, optionally substituted alkyl, alkenyl, alkoxy, alkenyloxy, alkylthio, cycloalkyl, amino, phenyl, carboxy, alkoxycarbonyl, carbamoyl, sulfo, alkylsulfonyl or sulfamoyl;
$R_2$, $R_3$, $R_4$, $R_5$ and $R_6$ are H, halogen, nitro, cyano, thiocyano, formyl, optionally substituted alkyl, alkenyl, cycloalkyl, alkylcarbonyl, amino, phenyl, carbamoyl, sulfo, alkoxysulfonyl or sulfamoyl; and
X is O or S.

SUMMARY OF THE INVENTION

The present invention relates to pyridinyloxy-(pyrimidinyloxy)benzene derivatives of Formula I, to herbicidal compositions containing them as active ingredient and to methods of using the compounds to control undesirable vegetation.

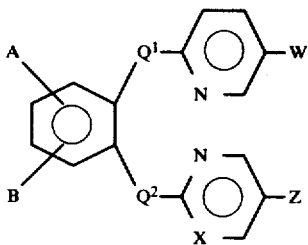

(I)

wherein
A is H, NO₂, F, Cl or Br;
B is H, C₁–C₄ alkyl, C₃–C₆ alkenyl, halogen, NO₂, CN, CHO, OR¹, COR¹, CO₂R¹ or SCN;
Q¹ is O or S;
Q² is O or S;
X is N or CH;
W is H, C₁–C₄ alkyl, C₃–C₄ alkenyl, F, Cl, Br, NO₂, CN, CF₃ or CO₂R²;
Z is H, C₁–C₄ alkyl, C₃–C₄ alkenyl, F, Cl, Br, NO₂, CN, CO₂R³ or CF₃; and
R¹, R² and R³ are independently C₁–C₄ alkyl.

Preferred for their high level of activity and/or ease of synthesis are those compounds of Formula I wherein:
A is H;
B is H, Cl, CH₃ or NO₂;
Q¹ is O;
Q² is O;
X is N or CH;
W is F, Cl, Br, NO₂ or CF₃; and
Z is F, Cl, Br or NO₂.

More Preferred for their higher level of activity and/or greater ease of synthesis are those compounds of the preferred group in which:
A is H;
B is H;
W is Cl or NO₂; and
Z is Br, Cl or NO₂.

The following compounds are specifically preferred for their excellent herbicidal activity and/or greatest ease of synthesis:
2,2'-[1,2-phenylenebis(oxy)]bis[5-chloropyridine];
5-bromo-2-[2-(5-chloropyridin-2-yloxy)phenoxy]pyrimidine;
5-chloro-2-[2-(5-nitropyridin-2-yloxy)phenoxy]pyridine;
5-chloro-2-[2-(5-chloropyridin-2-yloxy)phenoxy]pyrimidine; and
5-chloro-2-[2-(5-nitropyridin-2-yloxy)phenoxy]pyrimidine.

This invention also relates to an improved process for preparing ortho-(pyridin-2-yloxy)phenols comprising heating to a melt, under an inert atmosphere, a mixture of catechol and a halopyridine.

DETAILED DESCRIPTION OF THE INVENTION

Synthesis

The compounds of Formula I can be prepared by several different routes, depending on the particular substituents desired in the positions occupied by X, W and Z.

Compounds of Formula I, wherein the substituents W and Z are different, can be made according to Equation 1. An appropriately substituted catechol (Q¹,Q²=O), dimercaptobenzene (Q¹,Q²=S), or mercaptophenol (Q¹=S,Q²=O) of Formula II is allowed to react with an equimolar amount of a pyridine of Formula III wherein Y is a leaving group such as chlorine, bromine, alkylsulfonyl, or iodine to give a pyridin-2-yloxyphenol (Q²=O), pyridin-2-ylthiophenol (Q²=O) or a mercaptan of Formula IV.

Equation 1

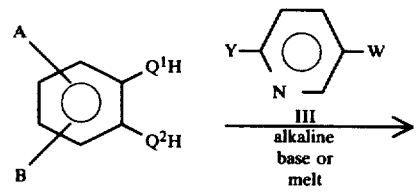

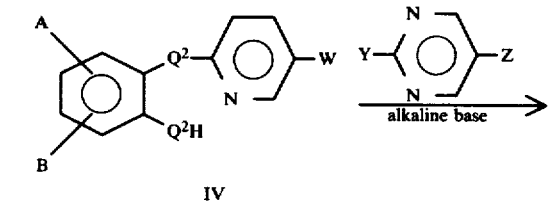

The condensation is generally carried out in the presence of an alkali material such as sodium hydroxide, potassium hydroxide, sodium carbonate, potassium carbonate, sodium methoxide, or potassium t-butoxide. However, the pyridin-2-yloxyphenol IV can also be obtained by simply heating the catechol of Formula II and an equimolar amount of the pyridine of Formula III as a melt.

Suitable solvents for this reaction include dimethylformamide, dimethylsulfoxide, sulfolan, dimethylacetamide, methyl ethyl ketone, and methyl isobutyl ketone. The reaction is preferably carried out at a temperature in the range of about 25° C. to 150° C. and a reaction time of about 1 to 24 hours. Usually, heating facilitates the reaction.

The present invention includes the improved process for preparing an ortho-(pyridin-2-yloxy)phenol of Formula VI from catechol and a 2-chloropyridine, such as 2,5-dichloropyridine, by heating the ingredients as a melt at about 150° C. under nitrogen, no alkaline material or cosolvent being necessary.

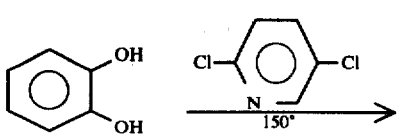

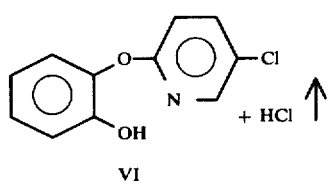

The pyridin-2-yloxyphenol ($Q^2=O$) or mercaptan ($Q^2=S$) of Formula IV can then be allowed to react with a preferably equimolar amount of the pyrimidine (X=N) or pyridine (X=CH) of Formula V, wherein Y is a leaving group such as chlorine, bromine, alkylsulfonyl, or iodine to yield the bis(pyridinyloxy)-benzenes, pyridinylthio(pyrimidinyloxy)benzenes, bis(pyridinylthio)benzenes, or pyridinylthio(pyrimidinyloxy)benzenes of Formula I. The condensation is generally carried out in the presence of an alkali material such as sodium hydroxide, potassium hydroxide, sodium carbonate, or potassium carbonate. Appropriate solvents for the reaction include dimethylformamide, ethyl methyl ketone, acetonitrile, dimethylsulfoxide, sulfolan, dimethylacetamide, or methyl isobutyl ketone. Preferably, the reaction is carried out at a temperature in the range of about 25° C. to 150° C. and a reaction time of about 1 to 24 hours.

An alternative method of synthesizing compounds of Formula I wherein X=N is shown in Equation 2. A suitably substituted catechol ($Q^1,Q^2=O$), dimercaptobenzene ($Q^1,Q^2=S$), or mercaptophenol ($Q^1=S,Q^2=O$) of Formula II is allowed to react with an equimolar amount of a pyrimidine of Formula IX, wherein Y is a leaving group such as chlorine, bromine, alkyl sulfonyl, or iodine to yield a pyrimidin-2-yloxyphenol ($Q^2=O$) or mercaptan ($Q^2=S$) of Formula X. Ordinarily, the reaction is carried out in the presence of an alkali material such as sodium hydroxide, potassium hydroxide, sodium carbonate, potassium carbonate, or sodium hydride and a suitable solvent such as dimethylformamide, dimethylsulfoxide, or methyl ethyl ketone. The temperature of the reaction can be in the range of about 25° C. to 150° C. with a reaction time of about 1 to 24 hours.

Subsequently, the pyrimidinyloxyphenol, pyrimidinylthiophenol, or the corresponding mercaptan of Formula X is combined with a pyridine of Formula III to yield the pyrimidinyloxy or pyrimidinylthiobenzene of Formula VIII as illustrated in Equation 2.

Equation 2

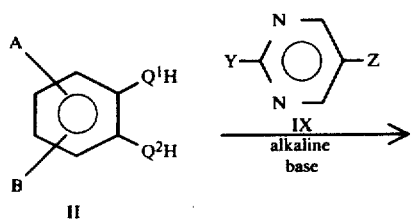

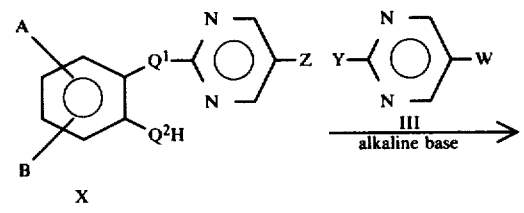

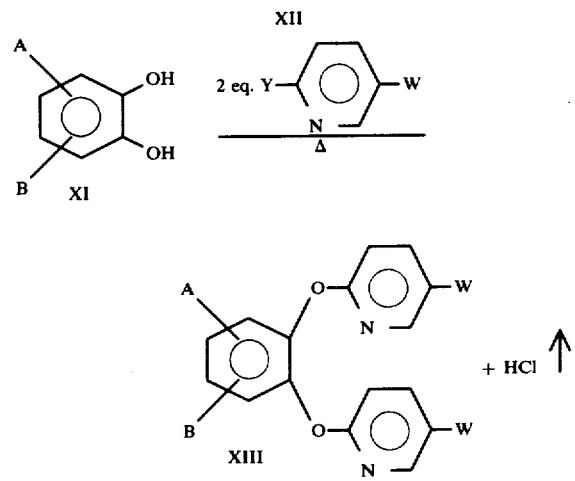

With compounds of Formula I, wherein X=CH, $Q^1$ and $Q^2=O$, and the substituents W and Z are the same, the reaction outlined in Equation 3 can also be used in their synthesis. An appropriately substituted catechol of Formula XI and two equivalents of the pyridine of Formula XII are heated as a melt under nitrogen with hydrogen chloride being driven off. As a result, the bis(pyridin-2-yloxy)benzenes of Formula XIII can be obtained directly.

Equation 3

The 2-halopyridines and 2-halopyrimidines used in these reactions can be prepared by methods known in the art (See for example, "The Pyrimidines" *Heterocyclic Compounds*, Chapter VI (1962); "Pyrimidine and its Derivatives" *Heterocyclic Compounds*, Elderfield, Chapter 7 (1957); "The Pyridines" *Heterocyclic Compounds*, Part II, Chapter VI (1960)).

As described in the *Journal of Organic Chemistry* 25, 1916 (1960), 2,5-dichloropyrimidine can be made according to the following method:

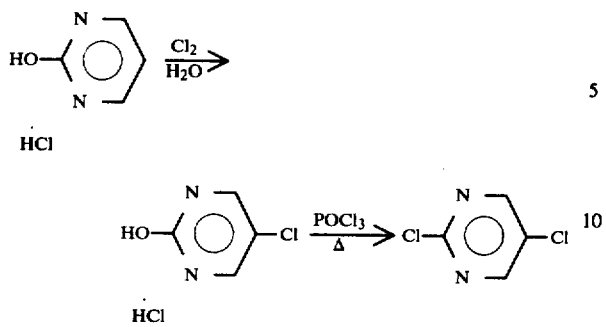

HCl

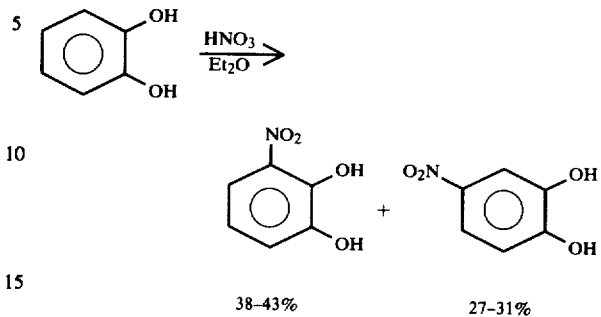

HCl

By reacting with an aqueous solution of chlorine, 2-hydroxypyrimidine hydrochloride was converted to 2-hydroxy-5-chloropyrimidine. Heating the 2-hydroxy-5-chloropyrimidine in excess phosphorous oxychloride gave 2,5-dichloropyrimidine.

Alternatively, 2-chloro-5-nitropyridine can be prepared using the procedure described in the *Journal Chemical Society* 9 (1941), starting with 2-aminopyrimidine. Nitration of 2-aminopyridine gives 2-amino-5-nitropyridine, which can be converted into 2-hydroxy-5-nitropyridine by a diazonium reaction. Subsequent heating of 2-hydroxy-5-nitropyridine in a phosphorous pentachloride/phosphorous oxychloride mixture yields 2-chloro-5-nitropyridine. The synthesis is summarized below:

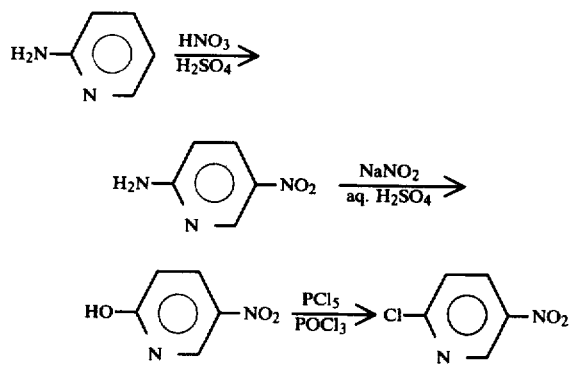

Preparations of the substituted catechols used in these reactions can also be found in the art (*Reactions of Catechols*, Crown Zellerbach Corp., Bulletin, 1977).

For example, chlorination of catechol with either chlorine or sulfuryl chloride, *Berichte* 44, 2182 (1911), C.A. 5, 3433 (1911) gives 4-chlorocatechol as the major product, whereas excess halogen yields the 4,5-dichlorocatechol.

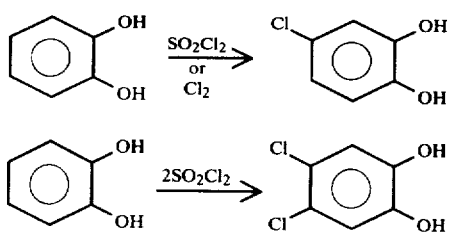

Nitration of catechol can be carried out under various conditions to yield the 3- and 4-nitrocatechols (*Journal Am. Chem. Soc.*, 75, 3277 (1953), *Journal Chemical Society*, 1088 (1971)).

[Reaction scheme: catechol + HNO₃/Et₂O → 3-nitrocatechol (38–43%) + 4-nitrocatechol (27–31%)]

The following examples illustrate the preparation of the compounds of this invention. Unless otherwise indicated, temperatures are in °C.

EXAMPLE 1

2-(5-Chloropyridin-2-yloxy)phenol

Under nitrogen, a mixture of 15.0 grams (0.136 mole) of catechol, and 22.0 grams of 2,5-dichloropyridine was heated as a melt at 140°–150° for 12 hours. The resulting black residue was dissolved in a minimum amount of methylene chloride, i.e., about 50 ml, chromatographed through a silica gel column using methylene chloride as the eluent. The 2-(5-chloropyridin-2-yloxy)phenol was isolated in the latter fraction, whereas starting material 2,5-dichloropyridine eluted with the solvent front. Yield 8.0 grams, m.p. 97°–100°; NMR (CDCl₃): δ6.70–7.70 (m's, ArH and OH), 8.0 (d, ArH); ir (Nujol): 3.20–2.80 (OH), 6.30 (C=N), 13.30 microns.

EXAMPLE 2

2,2'-[1,2-Phenylenebis(oxy)]bis[5-chloropyridine]

A mixture of 3.0 grams (0.027 mole) catechol and 9.0 grams (0.06 mole) 2,5-dichloropyridine was heated as a melt under nitrogen for 7 hours at 175° followed by heating at 200° for 5 hours. The black residue was dissolved in a minimum amount of methylene chloride and chromatographed through a silica gel column using methylene chloride as the eluent. From the initial fractions, the desired product was isolated. Yield 1.5 g, m.p. 82°–84°; NMR (CDCl₃): δ6.70 (d, 2H, ArH), 7.30 (s, 4H, ArH), 7.60 (AB quartet, 2H, ArH), 8.05 (d, 2H, ArH); ir (Nujol): 6.30 (C=N), 9.90, 11.95, 13.10 microns.

EXAMPLE 3

2,2'-[4-Methyl-1,2-phenylenebis(oxy)]bis[5-chloropyridine]

In 40 ml of dimethylformamide, a mixture of 4.0 grams (0.032 mole) 4-methylcatechol, 12.0 grams 2,5-dichloropyridine, and 12.0 grams of potassium carbonate was heated between 140° and 145° overnight. To the reaction mixture at room temperature was added excess H₂O and the resulting aqueous mixture was extracted with ethyl ether (200 ml) which was washed with H₂O (2X), saturated NaHCO₃, brine, dried (MgSO₄), filtered, and the solvent evaporated to yield an oil. Chromatography on a silica gel column using 1-chlorobutane as the eluent gave 5.0 grams of a white solid, m.p. 87°–90°; ir (Nujol): 6.30 (C=N), 9.10, 12.25 microns; NMR (CDCl₃): δ2.35 (s, 3H, CH₃), 6.60 (d, 2H, pyridine ring protons), 7.00 (broads, 3H, ArH), 7.45 (AB quartet, 2H, pyridine ring protons), 7.95 (d, 2H, pyridine ring protons).

EXAMPLE 4

5-Chloro-2-[2(5-nitropyridin-2-yloxy)phenoxy]pyridine

A mixture of 1.5 grams (0.0068 mole) 2-(5-chloropyridin-2-yloxy)phenol, 1.3 grams 2-chloro-5-nitropyridine, 1.0 grams potassium carbonate, and 40 ml of methyl ethyl ketone was heated at reflux overnight. Excess water was added and the aqueous mixture extracted with 200 ml of ethyl ether. The ether extract was washed with saturated $NaHCO_3$, $H_2O$, brine, dried ($MgSO_4$), filtered, and the solvent was evaporated to yield a solid which was suspended in hexane and filtered. Yield 1.4 grams, m.p. 82°-84°; ir (Nujol): 6.15, 6.25 (C=N, $NO_2$), 13.30 (broad), 13.70 microns; NMR ($CDCl_3$): δ6.55 (s, ArH), 6.75 (d, ArH), 6.95 (s, ArH), 7.35 (s, 4H, ArH), 7.40-7.65 (m, ArH), 8.05 (d, ArH), 8.40 (AB quartet, ArH), 8.95 (d, ArH).

Following the teachings of Examples 1, 2, 3 and 4 and by using the appropriately substituted catechols and pyridines, the title compounds in Table I can be prepared.

TABLE I
Bis(Pyridinyloxy)Benzenes

| A | B | W | Z |
|---|---|---|---|
| H | H | Cl | Br |
| H | H | Br | Br |
| H | H | $NO_2$ | Br |
| H | H | $NO_2$ | $NO_2$ |
| H | H | CN | CN |
| H | H | Cl | CN |
| H | H | Cl | F |
| H | H | F | F |
| H | H | Cl | $CF_3$ |
| H | H | $CF_3$ | $CF_3$ |
| H | H | H | H |
| H | H | Cl | H |
| H | H | $NO_2$ | $CF_3$ |
| H | H | $CH_3$ | $CH_3$ |
| H | H | Cl | $CH_3$ |
| H | H | Cl | $n-C_4H_9$ |
| H | H | Cl | $CH(CH_3)_2$ |
| H | H | $n-C_3H_7$ | $n-C_4H_9$ |
| H | H | Cl | $CH_2CH=CH_2$ |
| H | H | $CH_2CH=CH_2$ | $CH_2CH=CH_2$ |
| H | H | Cl | $CH_2CH=CHCH_3$ |
| H | H | $CH_2CH=CHCH_3$ | $NO_2$ |
| H | H | Cl | $CO_2CH_3$ |
| H | H | $CO_2CH_3$ | $CO_2CH_3$ |
| H | H | $CO_2-C_4H_9$ | Cl |
| H | H | CN | $CO_2-C_4H_9$ |
| 3-F | H | Cl | Cl |
| 3-$NO_2$ | H | CN | CN |
| 3-Cl | H | Cl | Cl |
| 3-Br | H | $NO_2$ | $NO_2$ |
| 3 or 6-F | H | Cl | $NO_2$ |
| 3 or 6-$NO_2$ | H | $NO_2$ | Br |
| 3 or 6-Cl | H | Cl | $NO_2$ |
| 3 or 6-Br | H | $CH_3$ | $NO_2$ |
| H | 4-$CH_3$ | Cl | Cl |
| H | 4-n-$C_4H_9$ | Cl | Cl |
| H | 4-$CH_2CH=CH_2$ | Cl | Cl |
| H | 4-$CH_2CH=CHCH_2CH_2CH_3$ | Cl | Cl |
| H | 4-Cl | Br | Br |
| H | 4-Br | Cl | Cl |
| H | 4-I | Cl | Cl |
| H | 4-$NO_2$ | Cl | Cl |
| H | 3-$CH_3$ | Cl | Cl |
| H | 4-CN | $NO_2$ | $NO_2$ |
| H | 4-CHO | $CH_3$ | $CH_3$ |
| H | 4-$OCH_3$ | Cl | Cl |
| H | 4-$OCH_2CH_2CH_2CH_3$ | Cl | Cl |
| H | 4-$COCH_3$ | Cl | Cl |
| H | 3-$COC(CH_3)_3$ | Cl | Cl |
| H | 4-$CO_2CH_3$ | CN | CN |
| H | 4-$CO_2C_4H_9$ | Cl | Cl |
| H | 4-SCN | Cl | Cl |
| 4-Cl | 5-Cl | $CH_3$ | $CH_3$ |

TABLE I-continued

Bis(Pyridinyloxy)Benzenes

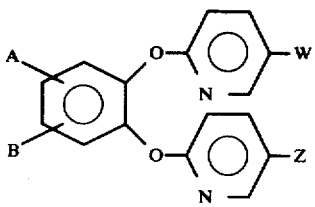

| A | B | W | Z |
|---|---|---|---|
| 4-NO$_2$ | 5-NO$_2$ | Cl | Cl |
| 3-NO$_2$ | 4-NO$_2$ | Cl | Cl |
| H | 4 or 5-CH$_3$ | Cl | NO$_2$ |
| H | 4 or 5-CH$_3$ | Cl | CF$_3$ |
| H | 3-CHO | CH$_3$ | CH$_3$ |
| H | 3-NO$_2$ | CN | CN |
| 3-NO$_2$ | 5-NO$_2$ | CH$_3$ | CH$_3$ |
| H | 4-C$_2$H$_5$ | Cl | Cl |
| H | 4-CH(CH$_3$)$_2$ | Cl | Cl |

EXAMPLE 5

2-(5-Chloropyrimidin-2-yloxy)phenol

To a mixture of 6.0 grams (0.055 mole) catechol and 7.0 grams of potassium carbonate stirring in 45 ml of dimethylformamide, 7.0 grams of 2,5-dichloropyrimidine was added and the mixture stirred at room temperature overnight followed by heating at 80° for 4 hours. Excess water was added to the reaction mixture, and the aqueous mixture extracted with 300 ml of ethyl ether. The ether extract was washed with H$_2$O (2X), brine, dried (magnesium sulfate), filtered, and the solvent removed to yield a yellow oil which slowly crystallized. From a 1-chlorobutane/cyclohexane mixture, the crude solid was recrystallized to give 6.0 grams of product, m.p. 131°–139°; ir (Nujol): 2.90–3.30 (OH), 12.80, 13.30 microns.

EXAMPLE 6

5-Bromo-2-[2-(5-chloropyridin-2-yloxy)phenoxy]-pyrimidine

To a mixture of 1.5 grams (0.0068 mole) 2-(5-chloropyridin-2-yloxy)phenol and 1.0 gram potassium carbonate stirring in 40 ml of methyl ethyl ketone, 1.6 grams of 2-chloro-5-bromopyridine was added and the mixture heated at reflux overnight. After addition of excess H$_2$O to the reaction mixture and extraction with 200 ml of ethyl ether, the ether extract was washed with H$_2$O, saturated HaHCO$_3$, brine, dried (MgSO$_4$), filtered, and evaporated to yield a yellow oil which crystallized from a 1-chlorobutane/cyclohexane mixture to give 1.3 grams of a white solid product, m.p. 93°–95°; ir (Nujol): 6.30 (C=N), 9,85, 10.45, 10.90, 11.25, 11.85, 12.40, 12.80, 13.10(s) microns; NMR (CDCl$_3$): δ6.70 (d, ArH), 7.30 (s, 4H, ArH), 7.45–7.65 (m, ArH), 8.0 (d, ArH), 8.50 (s, 2H, pyrimidine ring protons).

EXAMPLE 7

5-Chloro-2-[2-(5-chloropyridin-2-yloxy)phenoxy]-pyrimidine

With stirring, 1.80 grams (0.012 mole) of 2,5-dichloropyrimidine was added to a mixture of 2.0 grams (0.009 mole) 2-(5-chloropyridin-2-yloxy)phenol, 1.5 grams potassium carbonate, and 40 ml of methyl ethyl ketone. After the addition, the mixture was heated at reflux overnight and then poured into excess H$_2$O. After extracting with 200 ml of ethyl ether, the extract was washed with saturated NaHCO$_3$, H$_2$O, brine, dried (MgSO$_4$), filtered, and evaporated to yield a yellow solid which was recrystallized from 1-chlorobutane to give 2.3 grams of product, m.p. 108°–111°; ir (Nujol): 6.35, 6.50 (C=N), 13.20 microns; NMR (CDCl$_3$): δ6.75 (d, 1H, pyridine ring proton), 7.35 (s, 4H, ArH), 7.65 (AB quartet, 1H, pyridine ring proton), 8.10 (d, 1H, pyridine ring proton), 8.55 (s, 2H, pyrimidine ring protons).

EXAMPLE 8

5-Chloro-2-[2-(5-nitropyridin-2-yloxy)phenoxy]-pyrimidine

After heating at reflux a mixture of 1.5 grams (0.0067 mole) 2-(5-chloropyrimidin-2-yloxy)phenol, 1.2 grams potassium carbonate, 1.3 grams 2-chloro-5-nitropyridine and 40 ml of methyl ethyl ketone, the reaction mixture was poured into excess H$_2$0 and the aqueous mixture extracted with ethyl ether (200 ml). The ether layer was washed with saturated NaHCO$_3$, H$_2$O, brine, dried (MgSO$_4$), filtered, and evaporated to yield 2.3 grams of a yellow-orange oil which was purified by silica gel column chromatography (CH$_2$Cl$_2$as the eluent). NMR (CDCl$_3$): δ6.90 (d, 1H, pyridine ring proton), 7.35 (s, 4H, ArH), 8.25–8.50 (m, 1H, pyridine ring proton), 8.45 (s, 2H, pyrimidine ring protons), 8.95 (d, 1H, pyridine ring proton).

Following the procedure of Examples 5, 6, 7 and 8 and using suitably substituted catechols, pyridines, and pyrimidines, the following pyrimidinyloxybenzenes were prepared.

TABLE II

Pyrimidinyloxybenzenes

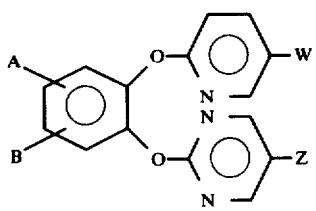

| A | B | W | Z |
|---|---|---|---|
| H | H | Cl | H |
| H | H | Cl | NO$_2$ |
| H | H | Br | CN |
| H | H | Cl | CH$_3$ |
| H | H | CN | Cl |
| H | H | H | Cl |
| H | H | NO$_2$ | Br |
| H | H | F | Cl |
| H | H | Cl | F |
| H | H | Br | Br |
| H | H | Cl | CF$_3$ |
| H | H | CF$_3$ | Cl |
| H | H | CH$_3$ | Cl |
| H | H | CH$_2$CH=CH$_2$ | Cl |
| H | H | Cl | CHCH=CH$_2$CH$_3$ |
| H | H | Cl | CH$_2$CH=CH$_2$ |
| H | H | Br | n-C$_4$H$_9$ |
| H | H | n-C$_4$H$_9$ | Cl |
| H | H | CH$_2$CH=CHCH$_3$ | Cl |
| H | H | CO$_2$CH$_3$ | Br |
| H | H | Cl | CO$_2$CH$_3$ |
| H | H | CO$_2$C$_4$H$_9$ | Cl |
| H | H | Cl | CO$_2$C$_4$H$_9$ |
| H | H | CH(CH$_3$)$_2$ | Cl |
| 3 or 6-F | H | Cl | Cl |
| 3 or 6-NO$_2$ | H | NO$_2$ | Cl |
| 3 or 6-Cl | H | NO$_2$ | Cl |
| 3 or 6-Br | H | Cl | Br |
| 3-NO$_2$ | 5-NO$_2$ | Cl | Br |
| 3-NO$_2$ | 4-NO$_2$ | NO$_2$ | Cl |
| 4-Cl | 5-Cl | Cl | Cl |
| 4-NO$_2$ | 5-NO$_2$ | NO$_2$ | Cl |
| H | 4 or 5-CH$_3$ | Cl | Cl |
| H | 4 or 5-n-C$_4$H$_9$ | Cl | Cl |
| H | 4 or 5-CH$_2$CH=CH$_2$ | CF$_3$ | Cl |
| H | 4 or 5-CH$_2$CH=CHCH$_2$CH$_2$CH$_3$ | NO$_2$ | Cl |
| H | 4 or 5-Cl | Br | Br |
| H | 4 or 5-Br | Cl | Cl |
| H | 4 or 5-I | NO$_2$ | Cl |
| H | 4 or 5-NO$_2$ | NO$_2$ | Br |
| H | 3 or 6-CH$_3$ | Cl | Cl |
| H | 4 or 5-CN | NO$_2$ | NO$_2$ |
| H | 4 or 5-CHO | Cl | Cl |
| H | 4 or 5-OCH$_3$ | Cl | Br |
| H | 4 or 5-OCH$_2$CH$_2$CH$_2$CH$_3$ | Cl | Cl |
| H | 4 or 5-COCH$_3$ | Cl | Cl |
| H | 3 or 6-COCH(CH$_3$)$_3$ | NO$_2$ | Br |
| H | 4 or 5-CO$_2$CH$_3$ | Cl | Cl |
| H | 4 or 5-CO$_2$C$_4$H$_9$ | Cl | Cl |
| H | 4 or 5-SCN | Cl | Cl |
| H | 4 or 5-CH$_3$ | NO$_2$ | Cl |
| H | 4 or 5-CH$_3$ | CF$_3$ | Cl |
| H | 3 or 6-CHO | Cl | Cl |
| H | 3 or 6-NO$_2$ | Cl | Cl |
| H | 4 or 5-C$_2$H$_5$ | Cl | Cl |
| H | 4 or 5-CH(CH$_3$)$_2$ | Cl | Cl |

EXAMPLE 9

5-Chloro-2-[2-(5-chloropyridin-2-ylthio)phenoxy]-pyridine

To a mixture of 3.0 grams (0.023 mole) of 2-mercaptophenol and 7.0 grams of potassium carbonate stirring in 50 ml of dimethylformamide, 9.0 grams of 2,5-dichloropyridine is added and the stirred mixture heated at 130° overnight. After pouring into excess H$_2$O, the aqueous mixture is extracted with ethyl ether (200 ml) and the extract washed with H$_2$O, saturated NaHCO$_3$, and brine, dried (MgSO$_4$), filtered, and the solvent evaporated to give the crude product which is recrystallized from 1-chlorobutane.

EXAMPLE 10

5-Nitro-2-[2-(5-chloropyridin-2-ylthio)phenoxy]pyridine

To a mixture of 3.0 grams (0.023 mole) of 2-mercaptophenol and 7.0 grams of potassium carbonate stirring in 50 ml of dimethylformamide, 4.0 grams of 2,5-dichloropyridine is added and the mixture stirred overnight at room temperature. After stirring overnight, 4.0 grams of 2-chloro-5-nitropyridine is added and the mixture is again stirred at room temperature overnight. Excess $H_2O$ is then added to the reaction mixture and the aqueous mixture extracted with ethyl ether (200 ml), washed with saturated $NaHCO_3$, $H_2O$, brine, dried ($MgSO_4$), filtered, and evaporated to yield the crude product.

By using the procedures described in Examples 9 and 10, the compounds listed in Table III can be prepared.

TABLE III
Pyridin-2-yloxy(pyridin-2-ylthio)benzenes

| A | B | W | Z |
|---|---|---|---|
| H | H | Br | Br |
| H | H | $NO_2$ | $NO_2$ |
| H | H | CN | CN |
| H | H | $CF_3$ | $CF_3$ |
| H | H | Cl | Br |
| H | H | Cl | H |
| H | H | Cl | F |
| H | H | F | Cl |
| H | H | H | Cl |
| H | H | $CH_3$ | $CH_3$ |
| H | H | $NO_2$ | Br |
| H | H | Cl | $CO_2CH_3$ |
| H | H | $CH_2CH=CH_2$ | Cl |
| H | H | Cl | $n-C_4H_9$ |
| 3-$NO_2$ | H | Cl | Cl |
| 3-Cl | H | Br | Br |
| 3-Br | H | Cl | Cl |
| H | 3-CHO | Cl | Cl |
| H | 4-$CH_3$ | Cl | Cl |
| H | 4-Cl | $CH_3$ | $CH_3$ |
| H | 4-Br | Cl | Cl |
| H | 4-CN | Cl | Cl |
| H | 4-$CH_2CH_3$ | Cl | Cl |

EXAMPLE 11

5-Nitro-2-[2-(5-chloropyrimidin-2-ylthio)phenoxy]-pyridine

At 0°, 4.0 grams (0.027 moles) of 2,5-dichloropyrimidine is added to a mixture of 3.0 grams (0.0023 mole) 2-mercaptophenol and 7.0 grams of potassium carbonate stirring in 50 ml of dimethylformamide. After stirring overnight at room temperature, 4.0 grams of 2-chloro-5-nitropyridine is added and the mixture is heated at 80° for 4 hours. The reaction mixture is then poured into excess $H_2O$ and extracted with ethyl ether (200 ml). Washing with $H_2O$, saturated $NaHCO_3$, brine, drying ($MgSO_4$), and evaporation yields the crude product.

Following the procedure described in Example 11, the following compounds in Table IV may be prepared.

TABLE IV
Pyrimidin-2-yloxy(pyridin-2-ylthio)benzenes

| A | B | W | Z |
|---|---|---|---|
| H | H | $NO_2$ | Br |
| H | H | Cl | Cl |
| H | H | $CF_3$ | Br |
| H | H | Cl | $NO_2$ |
| H | H | CN | Cl |
| H | H | $CH_3$ | $CH_3$ |
| H | H | H | Cl |
| H | H | Cl | F |
| H | H | F | Cl |
| H | H | Cl | $CO_2CH_3$ |
| H | H | Cl | $CH_2CH=CH_2$ |
| H | H | Cl | CN |
| 3-$NO_2$ | H | Cl | Cl |
| 3-Cl | H | $CH_3$ | $CH_3$ |
| 3-Br | H | Cl | Cl |
| H | 3-CHO | Cl | Cl |
| H | 4-$CH_3$ | Cl | Cl |
| H | 4-Cl | $NO_2$ | $NO_2$ |
| H | 4-Br | Cl | Cl |
| H | 4-$CH_2CH_3$ | Cl | Cl |
| H | H | H | H |

EXAMPLE 12

5-Chloro-2-[2-(5-nitropyridin-2-ylthio)phenoxy]-pyrimidine

At 0°, 4.0 grams (0.025 moles) of 2-chloro-5-nitropyridine is added to a mixture of 3.0 grams (0.0023 mole) 2-mercaptophenol and 7.0 grams of potassium carbonate stirring in 50 ml of dimethylformamide. After stirring overnight at room temperature, 4.0 grams of 2,5-dichloropyrimidine is added and the mixture is heated at 80° for 5 hours. The mixture is then poured into excess $H_2O$ and the aqueous mixture is extracted with ethyl ether (200 ml), washed with saturated sodium bicarbonate, brine, dried ($MgSO_4$), and the solvent is evaporated to yield the crude product.

The procedure in Example 12 may be modified and used in preparing the compounds listed in Table V.

TABLE V

Pyridin-2-ylthio(pyrimidin-2-yloxy)benzenes

[Structure: benzene ring with substituents A, B, and S-pyridine(W) and O-pyrimidine(Z) groups]

| A | B | W | Z |
|---|---|---|---|
| H | H | NO₂ | Br |
| H | H | Cl | Cl |
| H | H | Br | Br |
| H | H | Cl | CH₃ |
| H | H | CN | CN |
| H | H | Cl | NO₂ |
| H | H | CH₃ | CH₃ |
| H | H | Cl | H |
| H | H | H | Cl |
| H | H | CF₃ | Cl |
| H | H | Br | CF₃ |
| H | H | Cl | CO₂CH₃ |
| H | H | Cl | CH₂CH=CH₂ |
| 3-NO₂ | H | Cl | Cl |
| 3-Cl | H | CH₃ | CH₃ |
| 3-Br | H | NO₂ | NO₂ |
| H | 3-CHO | Cl | Cl |
| H | 4-CH₃ | Cl | Cl |
| H | 4-Cl | Cl | Cl |
| H | 4-Br | CH₃ | CH₃ |
| H | 4-CH₂CH₃ | Cl | Cl |
| H | 4-CN | Br | Br |
| H | H | H | H |

EXAMPLE 13

2,2'-[1,2-Phenylenebis(thio)]bis[5-chloropyridine]

In 50 ml of stirred dimethylformamide, a mixture of 3.0 grams (0.02 mole) dimercaptobenzene, 7.0 grams potassium carbonate, and 7.0 grams of 2,5-dichloropyridine is heated at 80° for 5 hours. Thereafter pouring into excess H₂O, the mixture is extracted with ethyl ether (200 ml) and washed with H₂O, saturated NaHCO₃, and brine, dried (MgSO₄), and evaporated to yield the crude product which can be recrystallized from 1-chlorobutane.

Example 13 illustrates the general procedure for preparing the compounds in Table VI.

TABLE VI

Bis(Pyridin-2-ylthio)benzenes

[Structure: benzene with A, B substituents and two S-pyridine groups bearing W and Z]

| A | B | W | Z |
|---|---|---|---|
| H | H | Br | Br |
| H | H | CF₃ | CF₃ |
| H | H | NO₂ | NO₂ |
| H | H | CN | CN |
| H | H | CH₃ | CH₃ |
| H | H | H | H |
| H | H | F | F |
| H | H | NO₂ | Cl |
| H | H | Cl | Br |
| H | H | CF₃ | Cl |
| H | H | NO₂ | CH₃ |
| H | H | CO₂CH₃ | Cl |
| 3-NO₂ | H | Cl | Cl |
| 3-Cl | H | Cl | Cl |
| 3-Br | H | CH₃ | CH₃ |
| H | 3-CHO | NO₂ | NO₂ |
| H | 4-CH₃ | Cl | Cl |
| H | 4-Cl | Cl | Cl |
| H | 4-Br | CH₃ | CH₃ |
| H | 4-CH₂CH₃ | Cl | Cl |
| H | 4-CN | Cl | Cl |

EXAMPLE 14

5-Bromo-2-[2-(5-chloropyrimidin-2-ylthio)phenylthio]-pyridine

To a mixture of 3.0 grams (0.02 mole) dimercaptobenzene and 7.0 grams of potassium carbonate stirring in 50 ml of dimethylformamide, 3.5 grams of 2,5-dichloropyrimidine is added at 0° and the mixture stirred for 4 hours, before adding 5.0 grams of 2,5-dibromopyridine and heating at 80° for 4 additional hours. The mixture is added to excess H₂O and extracted with ethyl ether. After washing the ether layer with H₂O, saturated NaHCO₃, brine, and drying (MgSO₄), evaporating the solvent gives the crude product.

Following the procedure of Example 14, the compounds in Table VII may be prepared.

TABLE VII

Pyridin-2-ylthio(pyrimidin-2-ylthio)benzenes

[Structure: benzene with A, B substituents, S-pyridine(W) and S-pyrimidine(Z) groups]

| A | B | W | Z |
|---|---|---|---|
| H | H | Cl | Cl |
| H | H | Br | Br |
| H | H | CH₃ | CH₃ |
| H | H | CF₃ | Cl |
| H | H | Cl | CO₂CH₃ |
| H | H | NO₂ | NO₂ |
| H | H | Cl | CN |
| H | H | CN | H |
| H | H | H | Cl |
| H | H | F | F |
| H | H | CH₃ | Cl |
| 3-NO₂ | H | Cl | Cl |
| 3-Cl | H | CF₃ | Cl |

TABLE VII-continued
Pyridin-2-ylthio(pyrimidin-2-ylthio)benzenes

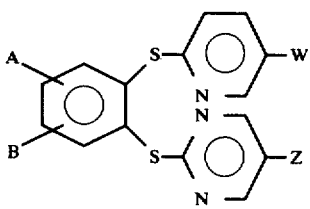

| A | B | W | Z |
|---|---|---|---|
| 3-Br | H | Cl | Cl |
| H | 3-CHO | NO$_2$ | Cl |
| H | 4-CH$_3$ | Cl | Cl |
| H | 4-Cl | CH$_3$ | Cl |
| H | 4-Br | Cl | Cl |
| H | 4-CH$_2$CH$_3$ | Cl | Cl |
| H | 4-CN | NO$_2$ | Br |

Formulations

The compounds of this invention can be formulated in a variety of ways for use. For example, the compounds can be formulated as dusts, granules, pellets, solutions, suspensions, emulsions, wettable powders, emulsifiable concentrates and the like. Many of the formulations can be applied directly to the area of undesirable vegetation. Sprayable formulations, on the other hand, can be extended in suitable media and used at spray volumes of from a few liters to several hundred liters per hectare. High strength compositions are used primarily as intermediates for subsequent formulation.

The formulations, according to this invention will ordinarily contain from about 0.1% to 80% by weight of active ingredient(s) and at least one of (a) about 0.1% to 20% surfactant(s) and (b) about 1% by 99.9% solid or liquid inert diluent(s). More specifically, they will contain these ingredients in the following approximate proportions:

TABLE VIII

| | Active* Ingredient | Inert Diluent(s) | Surfactant(s) |
|---|---|---|---|
| Wettable Powders | 20–80 | 0–74 | 1–10 |
| Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–80 | 20–99.9 | 0–15 |

*Active ingredient plus at least one of a Surfactant or a Diluent equals 100 weight percent.

Lower or higher levels of active ingredient can be used depending on the intended application and the physical properties of the compound. Higher ratios of surfactant to active ingredient are sometimes desirable, and the appropriate ration can be achieved by incorporating the surfactant into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annula", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of preparing the formulations are well known. Solutions can be prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon performed granular carriers or by agglomeration techniques. See J. E. Browning, "Agglomeration", *Chemical Engineering,* December 4, 1967, pp. 147ff. and "Perry's Chemical Engineer's Handbook", 5th Ed., McGraw-Hill, New York, 1973, pp. 8–57ff.

In the following examples, all parts are by weight unless otherwise indicated.

EXAMPLE 15

| Wettable Powder | |
|---|---|
| 5-chloro-2-[2-(4-chloropyridin-2-yloxy)phenoxy]-pyrimidine | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until practically all the solids are under 50 microns and then reblended.

EXAMPLE 16

| Wettable Powder | |
|---|---|
| 5-chloro-2-[2-(5-chloropyridin-2-yloxy)phenoxy]-pyrimidine | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles of active substantially all below about 10 microns in diameter. The product is reblended before packaging.

EXAMPLE 17

| Granule | |
|---|---|
| Wettable Powder of Example 16 | 5% |
| attapulgite granules (U.S.S. 20–40 mesh; 0.84–0.42 mm) | 95% |

A slurry of wettable powder containing about 25% solids is sprayed on the surface of attapulgite granules in a double-cone blender. The granules are dried and packaged.

EXAMPLE 18

| Extruded Pellet | |
| --- | --- |
| 2,2'-[1,2-phenylenebis(oxy)]bis[5-chloro-pyridine] | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 19

| Wettable Powder | |
| --- | --- |
| 5-chloro-2-[2-(5-chloropyridin-2-yloxy)phenoxy]-pyrimidine | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles substantially all below about 100 microns, the material is reblended and sifted through a U.S.S. No. 50 sieve (0.3 mm opening) and packaged.

EXAMPLE 20

| Low Strength Granule | |
| --- | --- |
| 2,2'-[1,2-phenylenebis(oxy)]bis[5-chloro-pyridine] | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to continue running for a short period, and then the granules are packaged.

EXAMPLE 21

| Aqueous Suspension | |
| --- | --- |
| 5-bromo-2-[2-(5-chloropyridin-2-yloxy)phenoxy]-pyrimidine | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles substantially all under 5 microns in size.

EXAMPLE 22

| Low Strength Granule | |
| --- | --- |
| 5-chloro-2-[2-(5-nitropyridin-2-yloxy)phenoxy]-pyridine | 0.1% |
| attapulgite granules (U.S.S. 20-40 mesh) | 99.9% |

The active ingredient is dissolved in a solvent, and the solution is sprayed upon dedusted granules in a double-cone blender. After spraying has been completed, the material is warmed to evaporate the solvent. The material is allowed to cool and then packaged.

EXAMPLE 23

| Granule | |
| --- | --- |
| 5-chloro-2-[2-(5-chloropyridin-2-yloxy)phenoxy]-pyrimidine | 70% |
| wetting agent | 1% |
| crude ligninsulfonate salt (containing 5-20% of the natural sugars) | 10% |
| attapulgite clay | 19% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 24

| Wettable Powder | |
| --- | --- |
| 5-bromo-2-[2-(5-chloropyridin-2-yloxy)phenoxy]-pyrimidine | 40% |
| sodium ligninsulfonate | 20% |
| montmorillonite clay | 40% |

The ingredients are thoroughly blended, coarsely hammer-milled and then air-milled to produce particles substantially all below 10 microns in size. The material is reblended and then packaged.

EXAMPLE 25

| Dust | |
| --- | --- |
| 2,2'-[1,2-phenylenebis(oxy)]bis[5-chloro-pyridine] | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 26

| Emulsifiable Concentrate | |
|---|---|
| 5-chloro-2-[2-(5-nitropyridin-2-yloxy)phenoxy]-pyrimidine | 20% |
| chlorobenzene | 74% |
| sorbitan monostearate and polyoxyethylene condensates thereof | 6% |

The ingredients are combined and stirred to produce a solution which can be emulsified in water for application.

UTILITY

The compounds of this invention are active herbicides. They have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures. By properly selecting rate and time of application, compounds of this invention may also be used to modify plant growth beneficially, and also to selectively control weeds in crops such as wheat, barley, sorghum, alfalfa, sunflower and corn.

The precise amount of the compounds of Formula I to be used in any given situation will vary according to the particular end result desired, the amount of foliage present, the weeds to be controlled, the crop species involved, the soil type, the formulation and mode of application, weather conditions, etc. Since so many variables play a role, it is not possible to state a rate of application suitable for all situations. Ordinarily, the compounds of this invention can be used at levels of about 0.01 to 20 kg/ha with a preferred range of 0.05 to 10 kg/ha. The higher rates from within this range are applied for particularly adverse conditions or where extended persistence in soil is desired.

The compounds of Formula I may be combined with other herbicides and are particularly useful in combination with the ureas: such as 3-(3,4-dichlorophenyl)-1,1-dimethylurea (diuron); the triazines: such as 2-chloro-4-(ethylamino)-6-(isopropylamino)-s-triazine (atrazine); the uracils: such as 5-bromo-3-sec-butyl-6-methyluracil (bromacil); N-(phosphonomethyl) glycine (glyphosate); 3-cyclohexyl-1-methyl-6-dimethylamino-s-triazine-2,4(1H,3H)-dione (hexazinone); N,N-dimethyl-2,2-diphenylacetamide (diphenamid); 2,4-dichlorophenoxyacetic acid (2,4-D) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl-diisopropylthiocarbamate (triallate); 1,2-dimethyl-3,5-diphenyl-1H-pyrazolium methyl sulfate (difenzoquat, methyl sulfate); methyl 2-[4-(2,4-dichlorophenoxy)-phenoxy]propanoate (diclofop methyl); 4-amino-6-tert-butyl-3-(methylthio)-1,2,4-triazin-5-(4H)-one (metribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); α,α,α-trifluoro-2,6-dinitro-N,N-dipropyl-p-toluidine (trifluralin); 1,1'-dimethyl-4,4'-bipyridinium ion (paraquat); monosodium methanearsonate (MSMA); 2-chloro-2',6'-diethyl (methoxymethyl) acetanilide (alachlor); 1,1-dimethyl-3-(α,α,α-trifluoro-m-tolyl)-urea (fluometuron); and 5-[2-chloro-4-(trifluoromethyl)phenoxy]-2-nitrobenzoic acid, methyl ester (acifluorfen-methyl).

The following examples further illustrate the herbicidal activity of the compounds of this invention.

Test A

Seeds of crabgrass (Digitaria spp.), barnyardgrass (Echinochloa crusgalli), wild oats (Avena fatua), cassia (Cassia tora), morningglory (Ipomoea sp.), cocklebur (Xanthium spp.), sorghum, corn, soybean, rice, wheat and nutsedge tubers (Cyperus rotundus) were planted in a growth medium and treated pre-emergence with the chemicals dissolved in a non-phytotoxic solvent. At the same time, cotton having five leaves (including cotyledonary ones), bush beans with the second trifoliate leaf expanding, crabgrass and barnyardgrass with two leaves, wild oats with one leaf, cassia with three leaves (including cotyledonary ones), morningglory and cocklebur with four leaves (including the cotylendonary ones), sorghum and corn with three leaves, soybean with two cotyledonary leaves, rice with two leaves, wheat with one leaf, and nutsedge with three to five leaves were sprayed. Treated plants and controls were maintained in a greenhouse for sixteen days, then all species were compared to controls and visually rated for response to treatment.

The ratings are based on a numerical scale extending from 0=no injury, to 10=complete kill. The accompanying descriptive symbols have the following meanings:

G = growth retardation;
C = chlorosis/necrosis;
S = albinism;
E = emergence inhibition;
6Y = abscised buds or flowers;
H = hormonal effects; and
— = not rated.

Compound 1

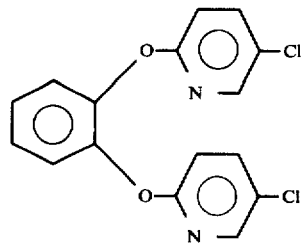

Compound 2

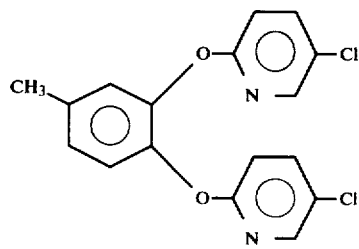

Compound 3

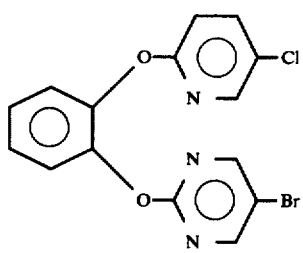

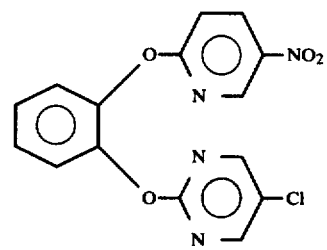

TABLE A

| Rate kg/ha | Compound 1<br>2 | Compound 2<br>0.4 | Compound 3<br>0.4 | Compound 4<br>0.4 | Compound 5<br>0.4 | Compound 6<br>0.4 |
|---|---|---|---|---|---|---|
| POST-EMERGENCE | | | | | | |
| Bush bean | 9S | 2C | 9S | 9S | 6S,6Y | 8C |
| Cotton | 6S | 4C | 5S | 4C,8G | 3C,8G | 8C |
| Sorghum | 3S | 0 | 0 | 1C,5G | 0 | 0 |
| Corn | 2C | 0 | 1S | 7C | 0 | 2C |
| Soybean | 8S | 2C | 5S | 9S | 2C,5G | 3S,5G |
| Wheat | 1C | 0 | 1C | 3C | 0 | 0 |
| Wild Oats | 7C | 0 | 1C | 8S | 0 | 0 |
| Rice | 7S | 0 | 0 | 5G | 0 | |
| Barnyardgrass | 9S | 7S | 5S 9S 2S | 2C | | |
| Crabgrass | 10S | 5C | 5S | 9S | 6S | 5C |
| Morningglory | 1S,5G | 7C | 7S | 9C | 0 | 7C |
| Cocklebur | 4S | 2C | 5S | 6S | 2C | 6C |
| Cassia | 8S | 4C | 6S | 5S,9G | 2C | 6C |
| Nutsedge | 3C | 0 | 0 | 2S | 0 | 0 |
| PRE-EMERGENCE | | | | | | |
| Sorghum | 9S | 4S | 9S | 9S | 5S | 9S |
| Corn | 6S,9H | 4S | 9S | 9S | 5S | 9S |
| Soybean | 5S | 0 | 8S | 8S | 1C | 8S |
| Wheat | 10S | 4S | 10S | 10S | 9S | 9S |
| Wild Oats | 10S | 6S | 9S | 10S | 9S | 9S |
| Rice | 8S | 5S | 9S | 8S | 6S | 6S |
| Barnyardgrass | 10S | 10S | 10S | 10S | 9S | 10S |
| Crabgrass | 10S | 9S | 9S | 10S | 9S | 9S |
| Morningglory | 5S | 0 | 6S | 10S | 0 | 10S |
| Cocklebur | 3C | 0 | 0 | 2C | 0 | 6G |
| Cassia | 10S | 0 | 9C | 10S | 0 | 10S |
| Nutsedge | 5S | 0 | 6C | 6S | 1C | 3C |

Compound 4

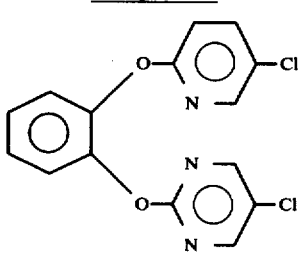

Compound 5

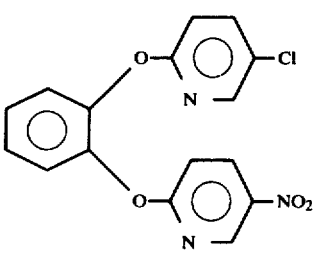

Compound 6

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

It may be seen that certain compounds from within the scope of the invention have utility for selective pre-emergence weed control in crops such as wheat, sorghum and corn.

kochia (*Kochia scoparia*), shepherd's purse (*Capsella bursa-pastoris*), *Matricaria inodora*, black nightshade (*Solanum nigrum*), yellow rocket (*Barbarea vulgaris*), wild mustard (*Brassica kaber*) and wild buckwheat (*Po-*

TABLE B

PRE-EMERGENCE ON FALLSINGTON SILT LOAM SOIL

| | Compound 1 | | Compound 3 | | Compound 6 | | Compound 4 (Series I) | | | | Compound 4 (Series II) | |
|---|---|---|---|---|---|---|---|---|---|---|---|---|
| Rate kg/ha | 1/4 | 1 | 1/8 | 1/2 | 1/8 | 1/2 | 1/32 | 1/16 | 1/4 | 3/4 | 1/8 | 1/2 |
| Crabgrass | 10C | 10C | 10C | 10C | 9C | 10C | 9C | 10C | 10C | 10C | 10C | 10C |
| Barnyardgrass | 10C | 10C | 7C | 10C | 6C | 10C | 2C | 10C | 10C | 10C | 9C | 10C |
| Sorghum | 0 | 2C | 0 | 0 | 2G | 5C | 0 | 0 | 5C | 10C | 1C | 7C |
| Wild Oats | 0 | 6C | 0 | 6C | 2C | 8C | 0 | 2C | 3C | 10C | 4C | 10C |
| Johnsongrass | 4G | 5C | 3G | 4C | 2C | 9C | 0 | 3G | 6C | 9C | 3C | 8C |
| Dallisgrass | 4C | 8C | 0 | 7C | 3C | 10C | 3G | 8C | 10C | 10C | 5C | 15S 8C |
| Giant Foxtail | 10C | 10C | 4G | 8C | 4C | 10C | 6C | 10C | 10C | 10C | 10C | 10C |
| Ky. bluegrass | 10E | 10E | 7C | 10C | 6C | 10C | 6C | 10C | 10C | 10C | 10C | 10C |
| Cheatgrass | 8E | 6E,4C | 5E | 10E | 0 | 7C | 5C | 5C | 5C | 9C | 0 | 7C |
| Sugarbeets | 10C | 10C | 10C | 10C | 9C | 10C | 10C | 10C | 10C | 10C | 10C | 10C |
| Corn | 0 | 3C | 0 | 0 | 3G | 0 | 0 | 0 | 0 | 0 | 0 | 2S |
| Mustard | 10C | 10C | 10E | 10E | 10C | 10C | 0 | 0 | 0 | 0 | 0 | 2S |
| Cocklebur | 0 | 0 | 0 | 0 | 0 | 3G | 0 | 0 | 0 | 3G | 0C | 0 |
| Pigweed | 9C | 9C | 10C | 10C | 8C | 10C | 10C | 10C | 10C | 10C | 10C | 10C |
| Nutsedge | 0 | 0 | 0 | 0 | 0 | 0 | 0 | 0 | 0 | 0 | 0 | 1S |
| Cotton | 0 | 1C | 0 | 3C | 2C | 5C | 0 | 1C | 5C | 10C | 3C | 10C |
| Morningglory | 0 | 0 | 0 | 2G | 0 | 10C | 0 | 0 | 0 | 3G | 0 | 1C |
| Cassia | 3C | 7C | 7C | 10C | 6C | 10C | 9C | 10C | 10C | 10C | 10C | 10C |
| Teaweed | 3C | 9C | 5C | 8C | 0 | 6C | 3C | 5C | 9C | 9C | 5C | 7C |
| Velvetleaf | 10C | 10C | 10C | 10C | 10C | 10C | 9C | 10C | 10C | 10C | 10C | 10C |
| Jimsonweed | 3C | 7C | 2C | 8C | 0 | 3C | 3C | 5C | 7C | 7C | 8C | 8C |
| Soybean | 2C | 5C | 0 | 6C | 2C | 5C | 0 | 4C | 8C | 9C | 5C | 9C |
| Rice | 3C | 7C | 0 | 4C | 4C | 5C | 2C | 6C | 9C | 9C | 8C | 9C |
| Wheat | 0 | 3C | 0 | 2C | 0 | 0 | 0 | 0 | 2C | 4C | 2C | 3C |

Test C

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descurainia pinnata*), smartweed (*Polygonum pensylvanicum*), tumble mustard (*Sisymbrium altissium*)

*lygonum convolvulus*). The above two pans were treated pre-emergence. At the same time two pans in which the above plant species were growing were treated post-emergence. Plant height at the time of treatment ranged from 1-15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table C. The potential utility of several of the compounds tested for pre- and/or post-emergence weed control in wheat and barley is evident.

TABLE C

| | Compound 1 | | Compound 2 | | | |
|---|---|---|---|---|---|---|
| Rate kg/ha | 1/2 PRE-EMERGENCE | POST-EMERGENCE | 1/16 PRE-EMERGENCE | 1/4 | 1/16 POST-EMERGENCE | 1/4 |
| Wheat | 0 | 0 | 0 | 0 | 0 | 0 |
| Barley | 1C,1G | 1C,1G | 0 | 0 | 0 | 0 |
| Wild Oats | 0 | 7C,6G | 0 | 0 | 0 | 0 |
| Downy Brome | 5C,4G | 6C,5G | 0 | 0 | 2G | 2C,5G |
| Cheatgrass | 7C,6G | 10C | 0 | 0 | 2G | 2C,4G |
| Blackgrass | 10C | 10C | 0 | 0 | 0 | 1G |
| Annual bluegrass | 10C | 10C | 2G | 4C,5G | 1C,4G | 5C,6G |
| Green foxtail | 10C | 10C | 1C,2G | 10C | 2C,3G | 10C |
| Quackgrass | 10C | 5C,6G | 0 | 1G | 1C,2G | 2C,3G |
| Italian ryegrass | 6C,4G | 7C,7G | 0 | 2G | 0 | 3G |
| Ripgut brome | 1G | 0 | 0 | 0 | 0 | 0 |
| Russian thistle | 0 | 2G | 0 | 0 | 0 | 1G |
| Tansy mustard | 10C | 10C | 10C | 10C | 10C | 10C |
| Smartweed | — | — | — | — | — | — |
| Tumble mustard | 10C | 10C | 2G | 10C | 10C | 10C |
| Kochia | 10C | 10C | 0 | 1G | 1C,2G | 3C,7G |
| Shepherd's purse | 10C | 10C | 2C,3G | 10C | 10C | 10C |
| *Matricaria inodora* | 4C,2G | 0 | 0 | 10C | 2G | 2C,4G |
| Black nightshade | 10C | 10C | 0 | 2C,4G | 2C,5G | 7C,8G |
| Yellow rocket | 10C | 10C | 2C,4G | 10C | 10C | 10C |
| Wild mustard | 10C | 10C | 7C,5G | 10C | 10C | 10C |

TABLE C-continued

| Rate kg/ha | Compound 1 | | Compound 2 | | | |
|---|---|---|---|---|---|---|
| | 1/2 | | 1/16 | 1/4 | 1/16 | 1/4 |
| | PRE-EMERGENCE | POST-EMERGENCE | PRE-EMERGENCE | | POST-EMERGENCE | |
| Wild buckwheat | 10C | 10C | 5C,4G | 7C,8G | 10C | 10C |

Test D

Twenty-five cm diameter plastic pots filled with Fallsington silt loam were planted with soybeans, cotton, alfalfa, corn, rice, wheat, sorghum, sugarbeets, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pensylvanicum*), crabgrass (Digitaria spp.), nutsedge (*Cyperus rotundus*), barnyardgrass (*Echinochloa crusgalli*), giant foxtail (*Setaria faberii*), mustard (*Brassica arvensis*), pigweed (*Amaranthus retroflexus*), sunflower (*Helianthus annuus*), and wild oats (*Avena fatua*). Approximately 2½ weeks after planting, the young plants and the soil around them were sprayed overall with the test chemicals dissolved in a non-phytotoxic solvent. Two weeks after treatment, all species were compared to untreated controls and visually rated for response to treatment. The rating system was as described previously for Test A. The data are presented in Table D. Selected compounds from within the scope of the invention have utility for post-emergence weed control in alfalfa, corn, wheat, sorghum and sunflower.

TABLE D

| | Over-the-Top Soil/Foliage Treatment | | | |
|---|---|---|---|---|
| | Compound 1 | | Compound 3 | |
| Rate kg/ha | 2 | 1/2 | 1 | 1/4 |
| Soybeans | 9G,8C | 9G,8C | 10C | 10C |
| Velvetleaf | 9G,9C | 10C | 10C | 9G,7C |
| Sesbania | 10C | 8G,8C | 10S | 9G,8C |
| Cassia | 10S | — | 10C | 10C |
| Cotton | 5G,5S | 4G,3S | 10C | 10C |
| Morningglory | 10S | 4G,4S | 10C | 10C |
| Alfalfa | 3C | 0 | 5G,7S | 2G,5S |
| Jimsonweed | 0 | 1S | — | 7G |
| Cocklebur | — | 2S | 6G,6S | 4G,6S |
| Corn | 1G,2S | 2S | 4G,5S | 3S |
| Crabgrass | 10C | 5G,5C | 10C | 10C |
| Rice | 10S | 5S | 9S | 5C |
| Nutsedge | 0 | 0 | 1C | 4G |
| Barnyardgrass | 10C | 3C | 10C | 3G,4C |
| Wheat | 1G,3C | 1C | 1G | 1G |
| Giant foxtail | 5S | 10S | 8G,6S | 2C |
| Wild Oats | 6G,6S | 3S | 6S | 0 |
| Sorghum | 1C | 0 | 8S | 2S |
| Mustard | 10S | 9G,9S | 10C | 10C |
| Pigweed | — | — | — | — |
| Johnsongrass | — | — | — | — |
| Sunflower | 2S | 2G,2S | 8G,5C | 3G,5S |

TABLE D-continued

| | Over-the-Top Soil/Foliage Treatment | | | |
|---|---|---|---|---|
| | Compound 1 | | Compound 3 | |
| Rate kg/ha | 2 | 1/2 | 1 | 1/4 |
| Sugarbeets | 10S | 10S | 10C | 10C |

What is claimed is:

1. A compound of the formula:

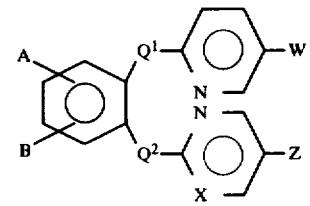

wherein
A is H, $NO_2$, F, Cl or Br;
B is H, $C_1$-$C_4$ alkyl, $C_3$-$C_6$ alkenyl, halogen, $NO_2$, CN, CHO, $OR^1$, $COR^1$, $CO_2R^1$ or SCN;
$Q^1$ is O or S;
$Q^2$ is O or S;
X is N or CH;
W is H, $C_1$-$C_4$ alkyl, $C_3$-$C_4$ alkenyl, F, Cl, Br, $NO_2$, CN, $CF_3$ or $CO_2R^2$;
Z is H, $C_1$-$C_4$ alkyl, $C_3$-$C_4$ alkenyl, F, Cl, Br, $NO_2$, CN, $CO_2R^3$ or $CF_3$; and
$R^1$, $R^2$ and $R^3$ are independently $C_1$-$C_4$ alkyl.

2. A compound of claim 1 wherein:
A is H;
B is H, Cl, $CH_3$ or $NO_2$;
$Q^1$ is O;
$Q^2$ is O;
X is N or CH;
W is F, Cl, Br, $NO_2$ or $CF_3$; and
Z is F, Cl, Br or $NO_2$.

3. A compound of claim 2 wherein:
A is H;
B is H;
W is Cl or $NO_2$; and
Z is Br, Cl or $NO_2$.

4. A compound of claim 1, 2,2'-[1,2-phenylenebis(oxy)]bis[5-chloropyridine].

5. A compound of claim 1, 5-bromo-2-[2-(5-chloropyridin-2-yloxy)phenoxy]pyrimidine.

6. A compound of claim 1, 5-chloro-2-[2-(5-nitropyridin-2-yloxy)phenoxy]pyridine.

7. A compound of claim 1, 5-chloro-2-[2-(5-chloropyridin-2-yloxy)phenoxy]pyrimidine.

8. A compound of claim 1, 5-chloro-2-[2-(5-nitropyridin-2-yloxy)phenoxy]pyrimidine.

* * * * *